United States Patent [19]

Weinberger et al.

[11] Patent Number: 5,037,523
[45] Date of Patent: Aug. 6, 1991

[54] AIR COOLED CARTRIDGE FOR CAPILLARY ELECTROPHORESIS

[75] Inventors: Scot R. Weinberger, Reno; Thomas W. Hoppe; Elia R. Tarantino, both of Sparks, all of Nev.

[73] Assignee: Spectra-Physics, Inc., San Jose, Calif.

[21] Appl. No.: 470,209

[22] Filed: Jan. 25, 1990

[51] Int. Cl.$^5$ .................. G01N 27/26; B01D 57/02
[52] U.S. Cl. .................. 204/299 R; 204/180.1
[58] Field of Search ............ 204/299 R, 180.1, 183.3

[56] References Cited

FOREIGN PATENT DOCUMENTS 339780 11/1987 European Pat. Off. ........ 204/299 R

OTHER PUBLICATIONS

Karger, B. L. et al., "High Performance Capillary Electrophoresis Using Open Tubes and Gels", Chromatographia, vol. 24 (1987), 15-24.
Nielsen, R. G. et al., "Capillary Zone Electrophoresis of Insulin and Growth Hormone", Analytical Biochemistry, vol. 177 (1989), 20-26.

Primary Examiner—John F. Niebling
Assistant Examiner—John S. Starsiak, Jr.
Attorney, Agent, or Firm—Skjerven, Morrill, MacPherson, Franklin & Friel

[57] ABSTRACT

An electrophoresis instrument includes a capillary tube mounted in an air cooled cartridge. The cartridge also supports a spherical lens which is part of the optical detection apparatus. The cartridge rests in a manifold which includes the sample and buffer reservoirs. The temperature of the capillary tube is controlled by measuring the electrical resistance of the capillary tube during the electrophoresis process and then cooling or heating the cartridge by circulating temperature controlled air over the tube. The optical path associated with the instrument is a fiber optic bundle bifurcated close to dual detectors into a reference arm and a sample arm so as to provide similar reference and sample optical paths. The instrument may be used for temperature control for gradient electrophoresis and also, a neutral marker for determining electro-osmotic flow may be detected.

4 Claims, 15 Drawing Sheets

AIR COOLED CARTRIDGE FOR CAPILLARY ELECTROPHORESIS

BACKGROUND OF THE INVENTION

1. Field of the Invention

This invention relates to an apparatus and method for performing capillary electrophoresis, and specifically to an air cooled cartridge for use in such an apparatus.

2. Description of the Prior Art

Capillary electrophoresis (CE) is a chemistry separation technique which utilizes the differences in solute electrophoretic velocity to isolate the various components of a sample. FIG. 1 depicts a typical CE apparatus. A high intensity electrical field supplied by high voltage power supply 10 is applied across a teflon, glass, or quartz separation capillary tube 12 of narrow inside diameter (5 to 400 micrometers) containing an electrolytic buffer solution. For an uncoated, open capillary tube, the presence of the electrical field imparts motion to charged and uncharged moieties present in the buffer through two mechanisms: electro-osmotic (endoosmotic) flow and electrophoretic force. Flow of buffer (or sample from sample vial 14) through capillary 12 is detected by a detector 16.

Electro-osmotic flow is the bulk flow of buffer from a first buffer vial 18 to a second buffer vial 19 through capillary 12 due to the shearing movement of a diffuse layer of cations past a more firmly held, dense layer interacting with integral, anionic groups of the capillary wall. Factors which influence the velocity of electroosmotic flow are: electrical field strength; buffer dielectric constant; zeta potential (the electrical potential existing between diffuse and compact cationic layers); and buffer viscosity (which is dependent on bulk properties of the buffer and the temperature of the buffer). For electro-osmotically driven, packed capillary, reverse phase chromatography applications, solvents of use are any normally used solvent for standard reverse phase liquid chromatography.

Electrophoretic force is the force applied to charged particles residing in an electrical field, and neutral or uncharged molecules are not affected. Positively charged molecules (cations) migrate towards the cathode while negatively charged molecules (anions) move towards the anode. Factors controlling solute electrophoretic velocity are: molecular charge; electrical field strength; viscosity of the migration media; and solute molecular geometric factors.

The net velocity at which a solute travels in an uncoated, open capillary tube during CE is the vector sum of the electro-osmotic and electrophoretic velocities. Buffer viscosity plays a significant role for both of these phenomenon. Both electrophoretic and electro-osmotic velocities are inversely proportional to buffer viscosity, thus affecting the net migration velocity for all solutes.

When an electrical field is applied to a capillary which contains buffer, joule heating occurs. Accordingly the temperature of the buffer within the capillary increases until a steady state of heat exchange between the capillary and its surrounding environment is achieved. Consequently the ultimate buffer temperature is dependent upon the ambient temperature surrounding the capillary. Because of the temperature dependence of viscosity, the mobility of a solute in a given buffer within a given capillary in a given electrical field is largely determined by ambient temperature. For temperatures between 15° to 30° C., a 1° C. temperature increase results in an approximate 2 percent decrease in viscosity, increasing solute net velocity by 2 percent.

As is the case in many chromatographic techniques, solute identity is linked to migration time and velocity. For one form of CE known as capillary zone electrophoresis, samples are loaded into the capillary as a slug or plug. The latter may be achieved by application of an electrical field or some hydrodynamic force (vacuum or pressure head). An electrical field is then applied and the solutes migrate, as bands, down the capillary at their respective net velocities. Differences among these velocities create the primary mechanism for solute separation. These solute bands are then detected by monitoring a bulk property of the buffer such as refractive index, photometric absorbance, fluorescence, electrical conductivity, or thermal conductivity. The time period extending from the initiation of the separatory process to the point of solute detection is termed the migration time. The net velocity is determined using the migration time and the distance traveled by the solute.

Because of the high efficiencies achieved in capillary electrophoresis, it is not uncommon to see peak widths as narrow as two to three seconds. For complex solute matrices, multiple peaks may be separated by as little as two to three seconds in migration time. Consequently, a twenty minutes CE run in which the temperature has changed by 0.1° C. can experience changes in migration time by as much as 2.4 seconds, possibly causing improper solute identification. Thus, efficient temperature regulation is required In the prior art, a capillary tube 12 as used in an electrophoresis instrument is supported in a variety of ways, depending on whether tube 12 is to be cooled by air, by liquid, or by metal plates in contact with the capillary tube. Cooling of tube 12 is important since the electrophoresis process subjects the capillary tube to a very high voltage which causes joule heating in the capillary tube. It is important to maintain the temperature of the tube at a stable predetermined temperature so as to be able to make measurements at a known temperature. Various schemes have been suggested for supporting and cooling the capillary tube, all of which have significant disadvantages and many of which are not suitable for air cooling purposes.

Prior art electrophoresis and similar spectrographic instruments typically include an optical path as shown in FIG. 2, which includes two light sources 22, 24 each of which provides a different spectra. Typically one light source 22 is a deuterium ($D_2$) source and the second light source 24 is a tungsten (W) light source. A movable shutter 26 is provided in front of light sources 22, 24 so as to switch in light source 22 or light source 24 depending on which spectra is desired. A light beam 28 from either light source is then passed through baffles 29 onto a concave holographic grating 30 or similar diffraction device, and then is focused into beam splitter 32 through baffles 33.

Beam splitter 32 in one form in the prior art is a short length of optical fibers. In the typical prior art instrument, a portion of the light transmitted to some of the optical fibers emerges from the beam splitter 32 at reference arm 34 and is sent via window 36 to a reference photodetector 38 which detects the reference light beam for purposes of comparison. The remainder of the light transmitted through beam splitter 32 is transmitted through a longer length of optical fibers to sample end 40 of the beam splitter and is focused using a lens 42 into sample cell 44 in which the sample is held. The portion of the light which passes through sample cell 44 and the sample therein is then directed onto a second (sample) photodetector 46 through window 48. The first and second photodetectors 38, 46 are matched substrate photodetectors, i.e. cut from the same piece of crystal or other photodetecting material, so as to have matching thermal properties. Also shown is monochromator casing 50. The dual beam approach compensates for fluctuations and the changes in intensity of the light source level, as well as any changes in intensity in the propagation of light.

For the purpose of remote detection in which only the sample arm is elongated, this prior art system has several disadvantages. Since reference photodetector 38 and sample photodetector 46 would be widely separated, they are subject to different amounts of heat due to their different locations. Thereby the problem of dark current i.e., drift caused by unequal heating, is significant, resulting in less precise measurements. Also, if the sample arm 40 of beam splitter 32 (i.e., that portion of the optical path which leads to the sample) is mechanically flexed, this flexing distorts the optical path through the optical fibers in sample arm 40, resulting in more or less light reaching sample cell 44. Since the portion of the light beam which reaches reference detector 38 is not so distorted, this causes a difference between the reference light beam and the sample light beam. Thereby, the prior art system is deficient because the common path of propagation is not maintained to the sample 46 and reference photodetectors 38.

Another significant problem with prior art electrophoresis instruments is the relative difficulty of controlling the temperature of the sample inside the capillary tube. As discussed above, capillary tubes are typically cooled by forced air or circulating liquid or by placing the capillary tube between metal radiator plates. The object is to cool and/or heat the capillary to a particular target temperature. Typically, the temperature control of the capillary tube in the prior art is performed by monitoring the temperature of the media surrounding the capillary tube. This process is problematic in that a thermal dam occurs at the interface between the media surrounding the capillary tube and the capillary tube itself. That is, thermal transfer is inhibited across this boundary, and therefore the temperature of the media surrounding the capillary tube is not exactly the same as that of the capillary tube itself.

As discussed above, electro-osmotic flow is the bulk flow of a solution to the capillary tube under high voltage which occurs in most forms of capillary electrophoresis in which the interior wall of the capillary tube has not been treated. It is well known that solutes move through the capillary tubing under the influence of the applied electric field at a net velocity equal to the vector sum of the electrophoretic velocity and the electro-osmotic velocity. Thus a cation, neglecting any solute-wall interactions, will have two mobilities or velocities in the same direction and thus will tend to move through the tubing relatively quickly. An anion will have an electrophoretic velocity which is the vector opposite direction of the electro-osmotic velocity and thus will tend to move through the capillary tubing relatively slowly. A non-charged species i.e., a neutral species, will have no electrophoretic velocity at all and thus can be used to measure the electro-osmotic velocity of the system. Typically amides or some other neutral species are used to measure electro-osmotic velocity. These materials are typically known as neutral markers The term neutral marker refers to the fact that in the buffer of interest, the neutral marker solute has no electrical charge.

In the prior art, electro-osmotic flow is determined by introduction of a neutral marker and then observing at one particular wavelength the flow of the neutral marker through the system to identify when the neutral marker passes the detector. This process works well with very simple sample combinations, where no other solutes co-migrate with the neutral marker If however other compounds present in the sample combination are also neutral, this complicates the process of detecting the neutral marker.

It is also known to detect electro-osmotic flow without the use of a neutral marker. In one known process, the electro-osmotic flow is determined by the level of current stabilization when different buffer solutions having different specific conductivities were provided in the anode and buffer reservoirs. This process relies on the assumption that the system demonstrates a zeta potential and dielectric constant which is not seriously affected by the change in the electrolyte composition in the solutes. In another method, electro-osmotic flow is determined without the use of a neutral marker by observing continuously the weight of the material held in the cathode buffer reservoir. The volume transfer is then determined by dividing the change in mass of the cathode buffer reservoir by the density of the buffer. These last two methods are extremely time consuming and difficult and require significant manual intervention in addition to being of doubtful accuracy. Thus, there is a significant need for a method to determine the electro-osmotic flow by an automated process which can deal with complex sample combinations.

SUMMARY OF THE INVENTION

In accordance with the invention, various improvements are made to an electrophoresis instrument for purposes of improving the accuracy and usability of the instrument and to allow measurements not obtainable using the prior art instruments.

In accordance with the invention, capillary tubing is coiled and enclosed in an air cooled cartridge. The air cooled cartridge includes a housing, electrodes fitted to the capillary tubing, and a spherical lens assembly which is part of the optical path. The air cooled cartridge holds the capillary tubing so as to optimize air cooling of the capillary tubing when the cartridge is installed in the instrument The air cooled cartridge fits into a manifold which includes both an anode and a cathode subassembly for holding vials containing the sample or buffer solutions and a ground potential chamber.

Also provided in accordance with the invention is a method of marking the air cooled cartridges using a bar code so as to provide identifying information for automated handling of the cartridges.

Also in accordance with the invention, a remote optical path is provided in which a fiber optic bundle having a particular arrangement of optical fibers for carrying the sample and reference light beams has an extended reference arm for carrying the reference light beam to the reference detector, which is located in close proximity to the sample photodetector. Thus the reference photodetector is in the same environment, i.e., heat level, as is the sample detector. This structure is advantageous in that remote transference of detection light in the common arm of the bifurcated optical fiber bundle reduces the optical system sensitivity to mechanical perturbations to the optical fibers. Thus slight changes are viewed simultaneously by both the sample and reference photodetectors and are thus more easily corrected.

In accordance with another aspect of the invention, the temperature of the capillary tubing during electrophoresis is controlled by observation of the electrical resistance of the capillary tubing. This method relies on the determination that the electrical resistance of the tubing containing a given buffer is a unique function of its temperature. Thus resistance may be calculated from the observed voltage and current across the capillary, and the capillary tubing may be air cooled by provision of an air flow across the capillary tubing in response to the observed resistance.

The provision in accordance with the invention of very precise reproducible temperature control provides the ability to perform thermal gradient electrophoresis in the instrument. It has not been possible previously to perform this process in a reliable, reproducible manner since the required temperature control equipment was not in existence.

Also in accordance with the invention, a method is provided of determining electro-osmotic flow by use of a neutral marker in which the spectral characteristics of the neutral marker are identified and used to determine when the neutral marker has passed the detector. The method of observation and determination of the spectrum associated with the neutral marker allows use of determination of electro-osmotic flow even in the case of co-elution or co-migration of a solute which is similar in its electrophoretical profile to that of the neutral marker.

BRIEF DESCRIPTION OF THE DRAWINGS

Similar reference numbers in various figures denote similar or identical structures.

DETAILED DESCRIPTION OF THE INVENTION

In accordance with the invention, various improvements are provided over the prior art electrophoresis apparatus.

Figure 3A:
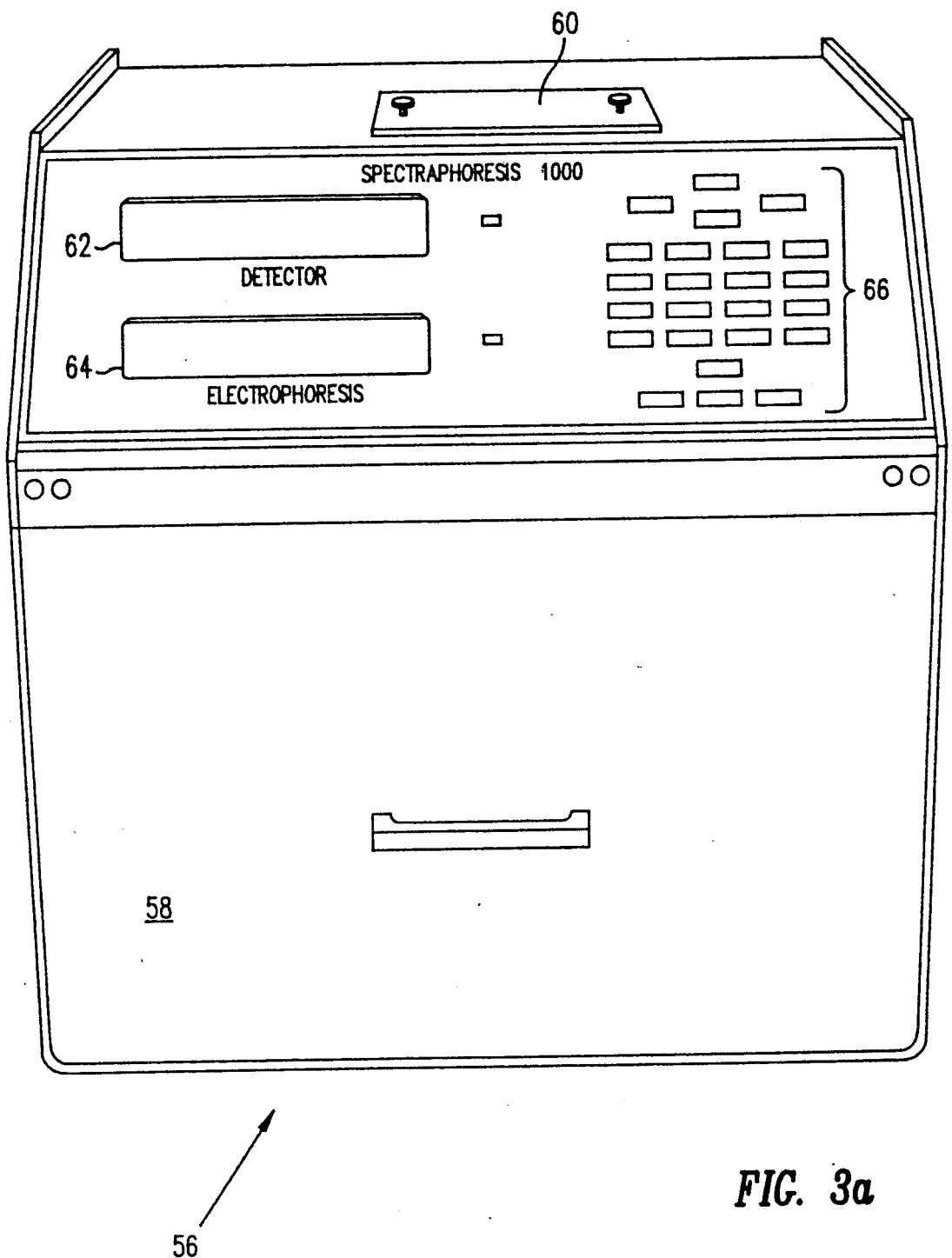
FIGS. 3(a) to 3(c) show views of an electrophoresis instrument in accordance with the invention.

FIG. 3(a) shows a front view of an electrophoresis instrument in accordance with the invention. Shown in enclosure 56 is the front panel 58 in a closed position, air cooled cartridge loading port 60, information displays 62, 64, and control buttons 66.

Figure 3B:
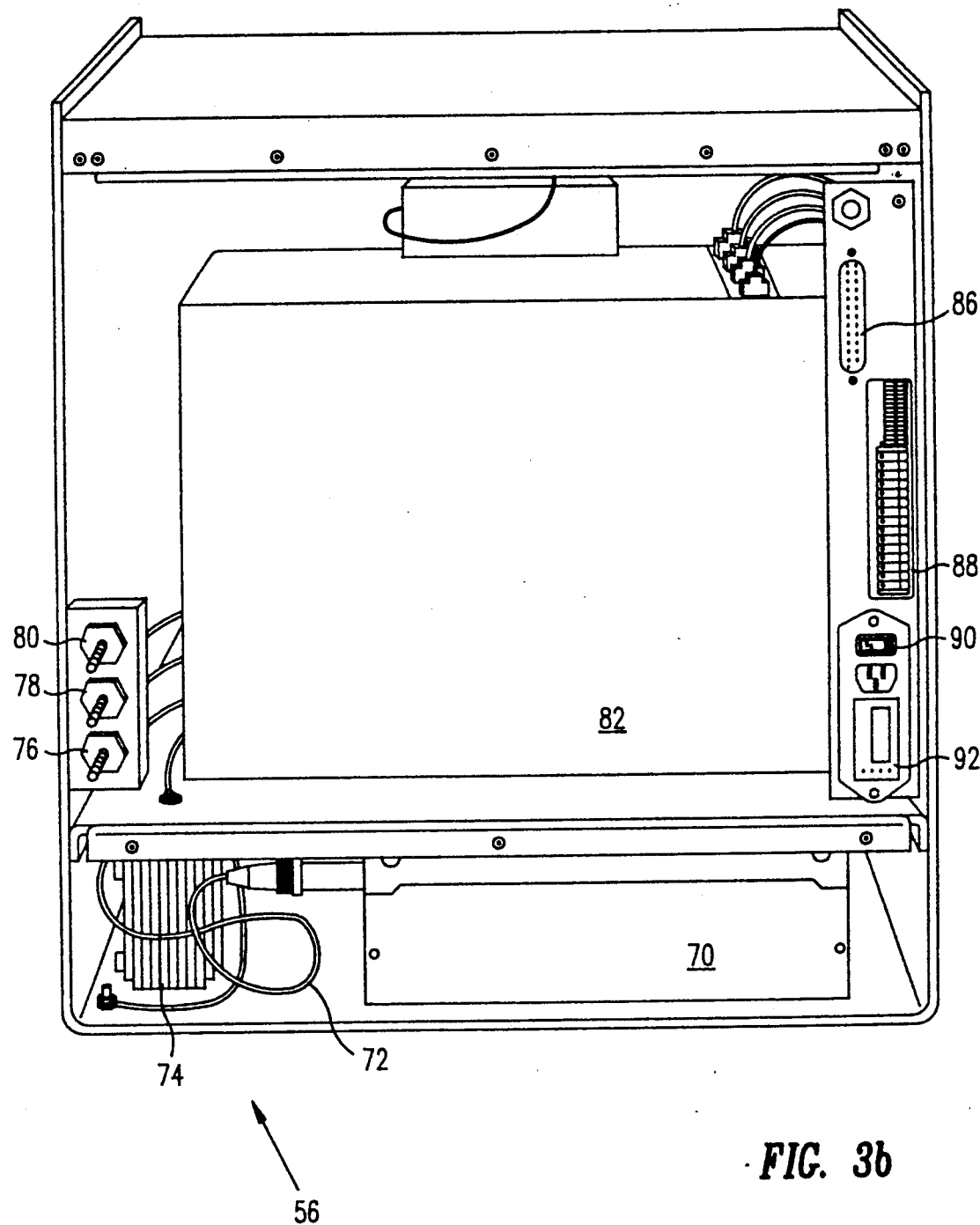

FIG. 3(b) shows a rear view of the instrument of FIG. 3(a). Shown in enclosure 56 are high voltage power supply 70, high voltage line 72, power transformer 74, vacuum exhaust port 76, oven purge port 78, and helium inlet port 80. The rear of the detector 82 portion of the instrument is shown. Also included are RS232 connector 86, I/O port 88, power switch 90, and voltage selector and fuse block 92.

Figure 3C:
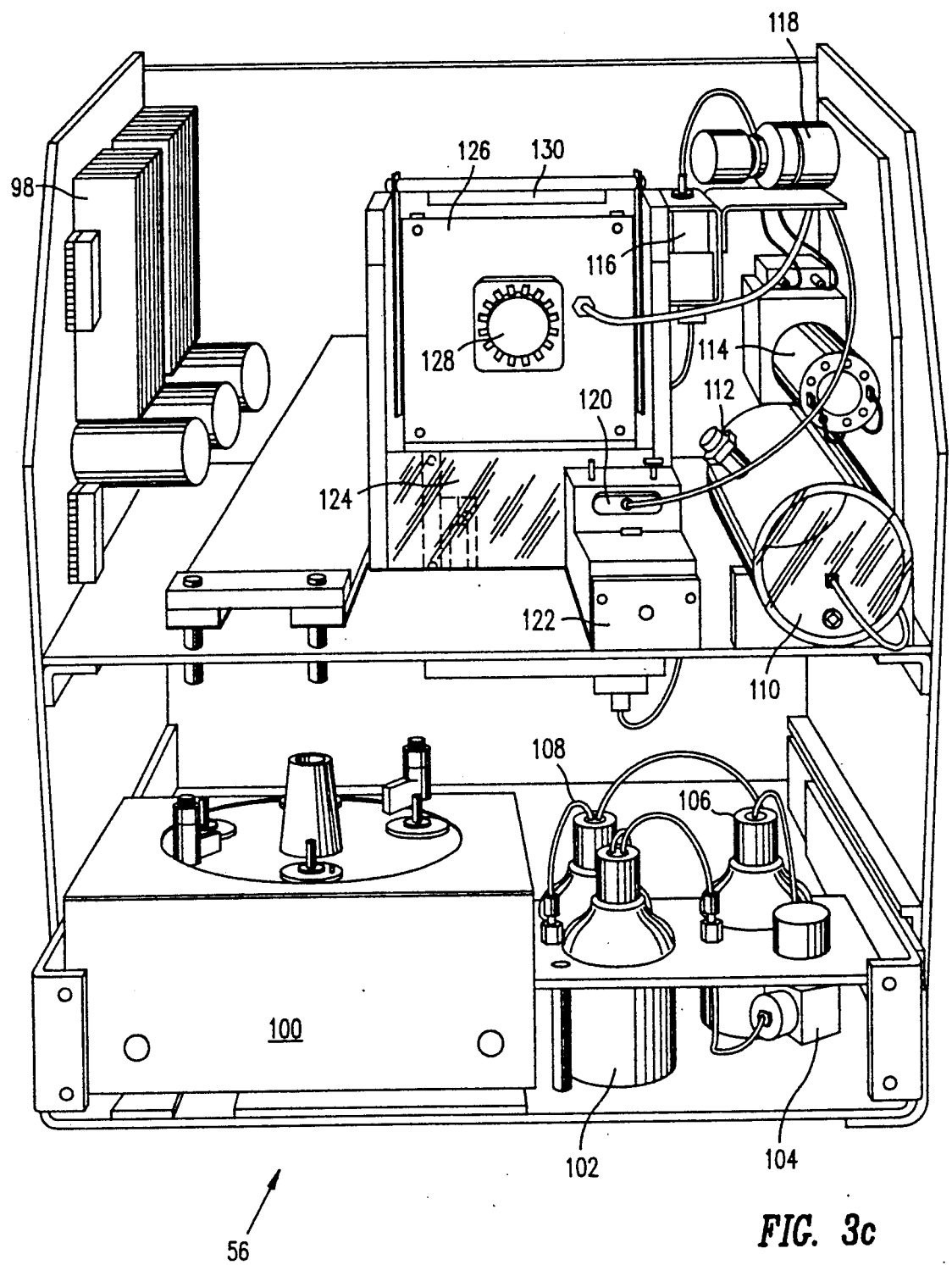

FIG. 3(c) shows a front view of the instrument of FIG. 3(a), with the front panel removed. Shown are electric power board 98, a conventional autosampler 100, buffer solution bottle 102, helium valve 104, dessicant bottle 106, waste trap 108, injection vacuum tank 110, pressure transducer 112, vacuum pump 114, fluid pump 116, valve 118, beam splitter 120, optical bench 122, manifold 124, oven (thermal chamber) 126, fan 128, and air cooled cartridge 130.

Figure 3D:
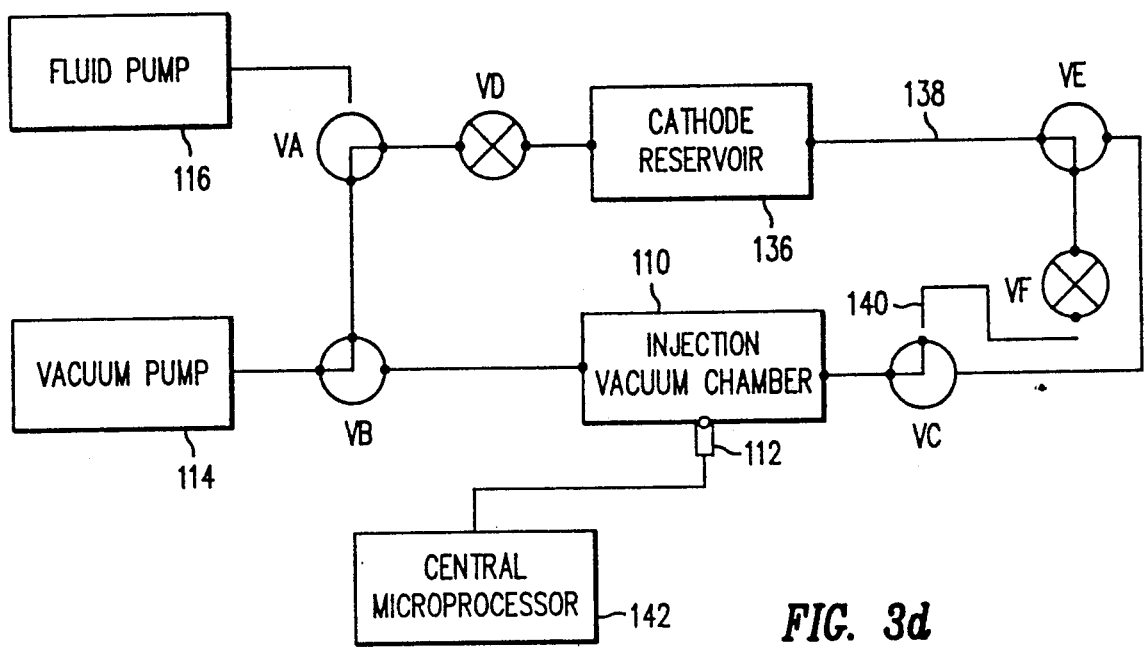
FIG. 3(d) shows schematically a column conditioning and hydrodynamic injection system in accordance with the invention.

FIG. 3(d) shows schematically a column conditioning and hydrodynamic injection system for the above described instrument in accordance with the invention. Shown are fluid pump 116, vacuum pump 114, valve VA, valve VB, valve VD, cathode reservoir 136, vent line 138, valve VE, valve VF, valve VC, atmospheric pressure line 140, injection vacuum chamber 110, pressure transducer 112, and control microprocessor 142.

Air Cooled Cartridge

An air cooled cartridge 130 (see FIG. 4) is used for capillary electrophoresis in accordance with the invention. Cartridge 130 consists of: a main body 146; a bobbin assembly 148; a spherical lens holder assembly 150; metallic electrodes 152, 154; electrical contacts 156, 158; and capillary tubing 162 of glass, quartz, or teflon, typically no greater than 500 microns in inside diameter and about 10 to 200 cm. long.

Main body 146 is a support for the other subassemblies. Additionally, main body 146 aligns the electrode 152, 154 and optical 150 subassemblies with their respective counterparts in the manifold and remote optical path (not shown here but described below).

Bobbin assembly 148 supports capillary 162 which is coiled in a concentric circle. Bobbin 148 consists of a central support ring 166 with radiating capillary support pieces 168, 170, etc. Each capillary support piece 168, 170, etc., contains four equally spaced holes (not shown) and one hole centered above the array of four, through which capillary 162 is threaded and held in place. The thickness of each support piece 168, 170 is minimized, maximizing the capillary surface area exposed to ambient air.

Spherical lens holder 150 fastens capillary 162 to the cartridge main body 130 prior to entry of capillary 162 to electrode 152 as well as holding capillary 162 in the proper orientation with spherical lens holder 150, permitting precise image focusing into the capillary lumen, thus limiting stray light. Spherical lens holder 150 mates with the remainder of the remote optical path (not shown) to provide precise, reproducible optical alignment, as described below.

Metallic electrodes 152, 154 are constructed of high conductivity, low electrochemical reactivity metals. An alloy of platinum-iridium is used in one embodiment. A portion of capillary 162 exits cartridge 130 and enters the manifold (not shown) by passing through the center of electrodes 152, 154. Electrodes 152, 154 each have an inside diameter slightly larger than that of the outside diameter of capillary 162. This minimizes the dead volume between electrodes 152, 154 and capillary 162.

Air cooled cartridge 130 is a structure approximately five inches (12 cm.) wide, nine inches (22 cm.) high, and 0.25 inch (0.5 cm.) thick. Main body 146 of the air cooled cartridge is preferably molded from black delrin. Other low thermal mass, low thermal conductivity, and high dielectric strength materials may be used. The dimensions of air cooled cartridge 130 may be otherwise as convenient. Air cooling slots 171-1, 171-2, ..., 171-n are formed in main body 146. Spherical lens holder 150 is preferably made of black UV stabilized ABS and is a flange-like structure with a smaller portion which fits inside a cavity provided in main body 146 and with a lip for fitting against main body 146 to fix lens holder 150 in place. Other high dielectric strength, UV stable materials may also be used for lens holder 150.

Bobbin assembly 148, around which capillary tube 162 is concentrically wound, is formed of delrin and is about 3.5 inches (9.0 cm.) in diameter and fits inside a cavity provided in main body 146.

Figure 5:
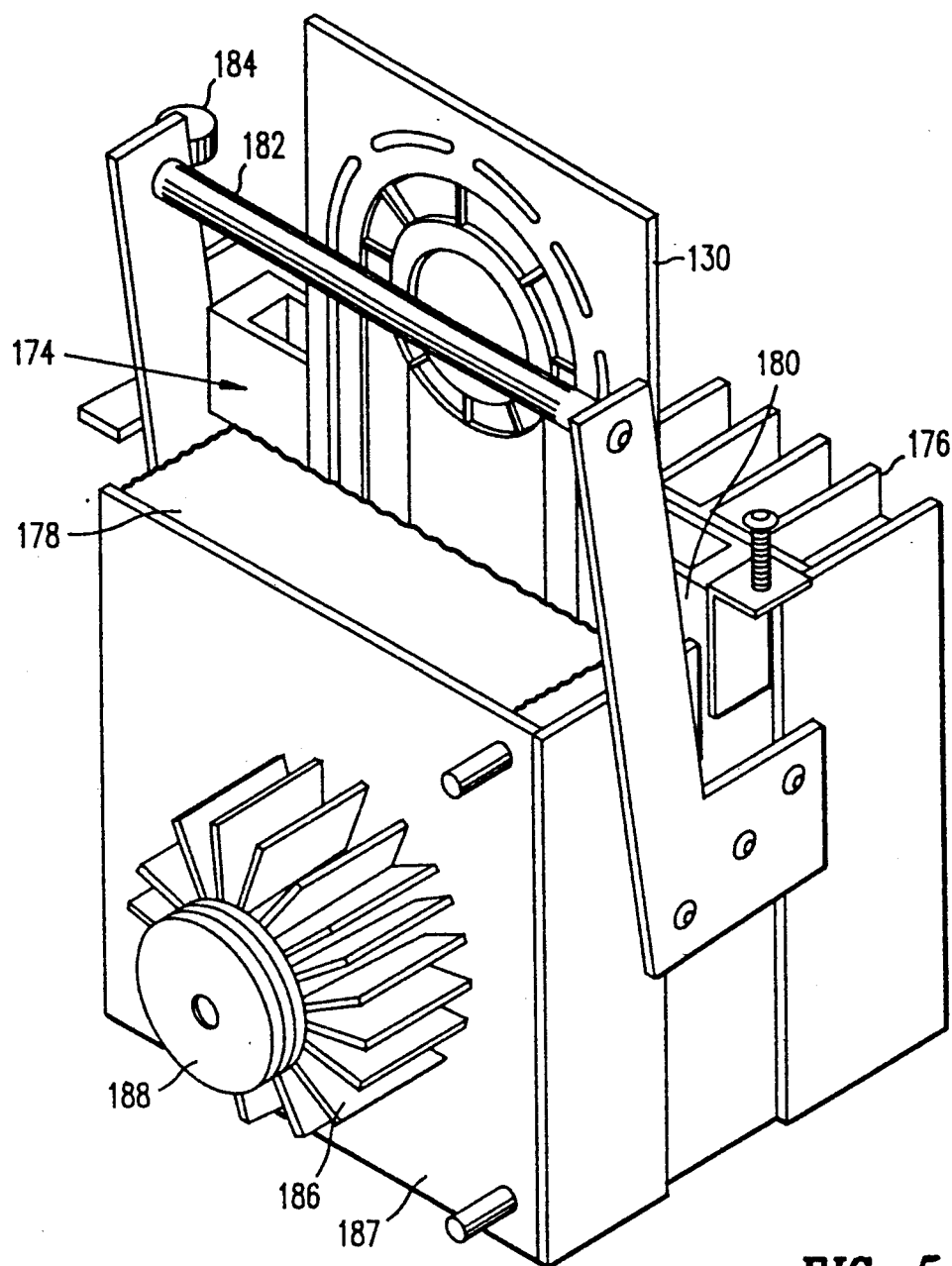
FIG. 5 shows the air cooled cartridge partially inserted into the temperature control system.

As shown in FIG. 5, air cooled cartridge 130 is partially lowered into a chamber 174 at one side of which is provided a Peltier type heat sink device 176, which is a well known type of solid state device for cooling and/or heating to precise temperatures. On each side of cartridge 130 is an insulative layer of polyethylene 178, 180, each layer 178, 180 approximately 0.78 inches (2.0 cm.) thick. Air cooled cartridge 130 when fully lowered into position between insulative layers 178, 180 is locked in place by a cartridge lock bar 182. A retaining thumb screw 184 is also provided. Also provided is a fan (the blades of which are hidden and not shown) mounted on panel 187 driven by a regulated DC motor 188 fitted with a heat sink assembly 186 for drawing the air cooled by Peltier heat sink 176 across the capillary (not shown) in cartridge 130.

Figure 6:
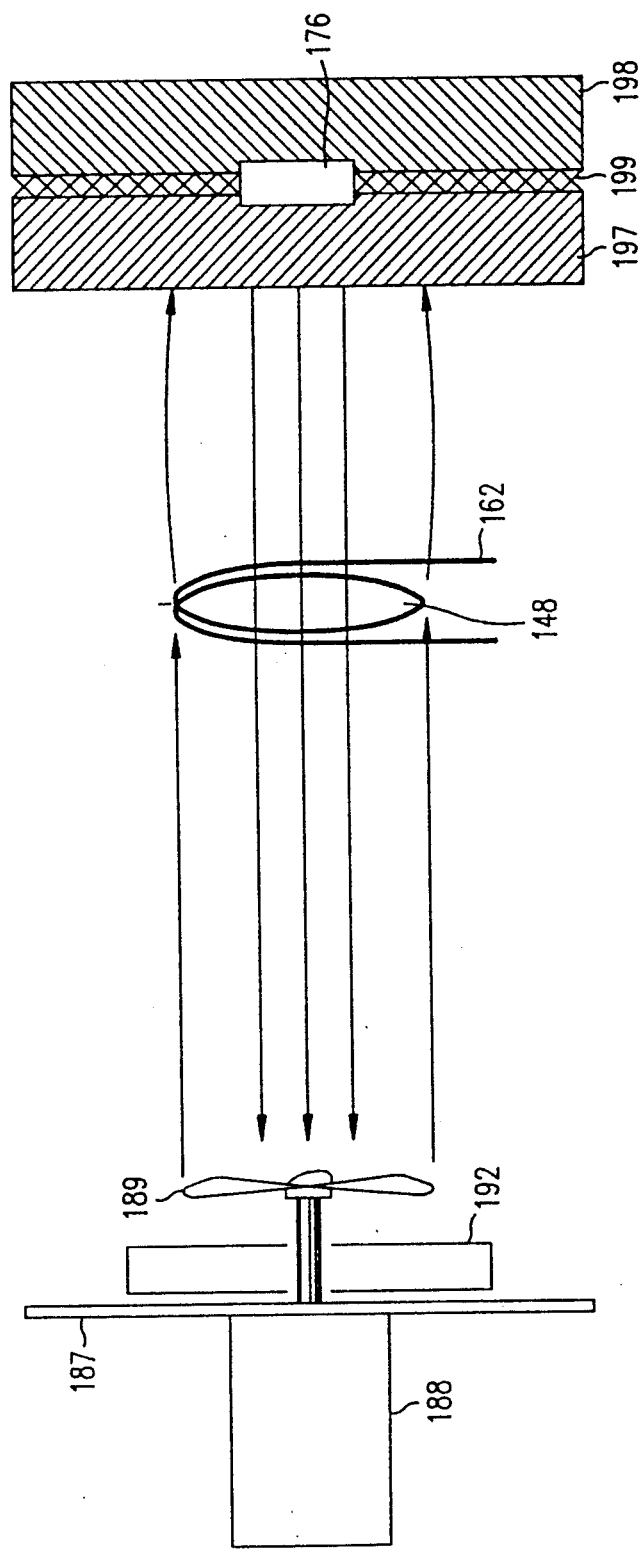
FIGS. 6 and 7 show a temperature control system in accordance with the invention.

The cooling system in accordance with the invention is shown schematically in FIG. 6 showing DC motor 188 for driving fan blades 189, and also installed on panel 187 supporting fan blades 189 is a temperature sensing, resistive thermal device 192 (RTD). As shown, fan blades 189 draw the air (shown by lines) through the center of bobbin 148. The air is then recirculated by fan blades 189 across capillary 162 to the temperature regulating heat exchange surface 197 of the Peltier device.

Peltier device 176 is sandwiched between conventional heat exchanging surface 197 and conventional heat dissipating/collecting surface 198. Surfaces 197, 198 are separated by a 0.25" (6.3 mm) thick layer of polyethylene insulation 199.

Figure 7:
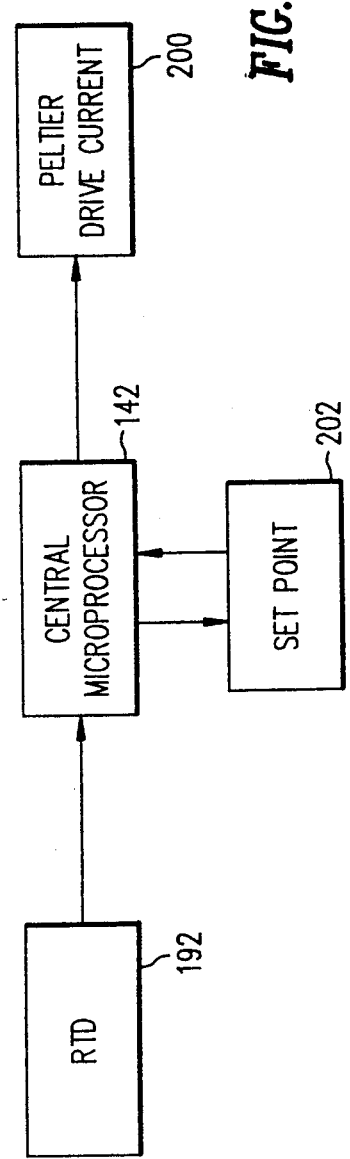

As shown in FIG. 7 in a block diagram, RTD device 192 provides a measurement of the temperature of air surrounding capillary 162. The capillary electrical resistance is determined by dividing the applied voltage (usually about 5 KV) by the measured current during a calibration phase. This resistance information is provided to microprocessor 142 which is part of the electrophoresis instrument and which in one embodiment is a Motorola 68008 microprocessor. This microprocessor then uses the ambient air temperature and capillary resistance data to control the drive current 200 to Peltier device 176 so as to maintain a constant electrical resistance and set point temperature 202 in capillary 162 during the separation process. The actual set point is the capillary resistance. Ambient temperature (not shown) is used as a secondary parameter to anticipate the arrival at the desired capillary resistance, thus minimizing set point setting time.

Figure 8:
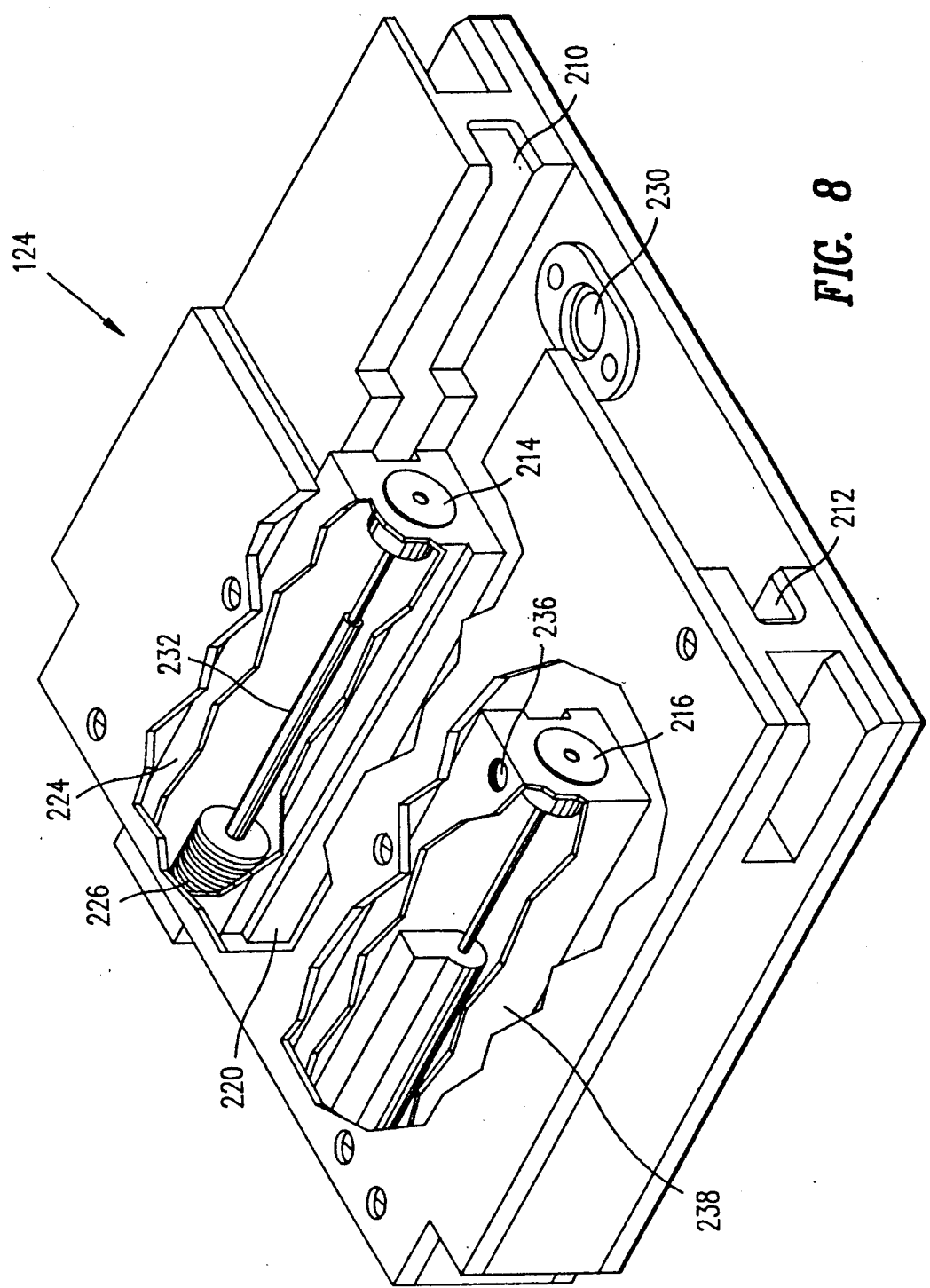
FIG. 8 shows a manifold in accordance with the invention.

The lower portion of the air cooled cartridge when in a lowered position is in contact with a manifold 124, as shown in FIG. 8. The air cooled cartridge (not shown) fits into alignment slots 210, 212. Manifold 124 includes a high potential (anode or cathode) subassembly, including high voltage contact 214, which accepts vials containing either sample solution or buffer solution and also includes a central support subassembly 220, and a ground potential chamber 224, containing high voltage contact 216, which is connected to a valve assembly via port 226 which allows (under automatic control) the filling and flushing with buffer and application of vacuum to the capillary tubing in the air cooled cartridge for the purpose of rinsing, washing, or hydrodynamic injection. These processes are performed by the structure shown schematically in FIG. 3(d). Also provided in manifold 124 is a hole 230 for the optical bench (not shown, described below) to slide into so as to contact the spherical lens assembly (not shown, in the air cooled cartridge). A vial-like chamber 232 is built into the manifold structure so as to eliminate the need for a ground potential buffer vial. Also provided are high voltage line entrance 236 and high potential vial holder 238.

Bar Code on Cartridge

Figure 4:
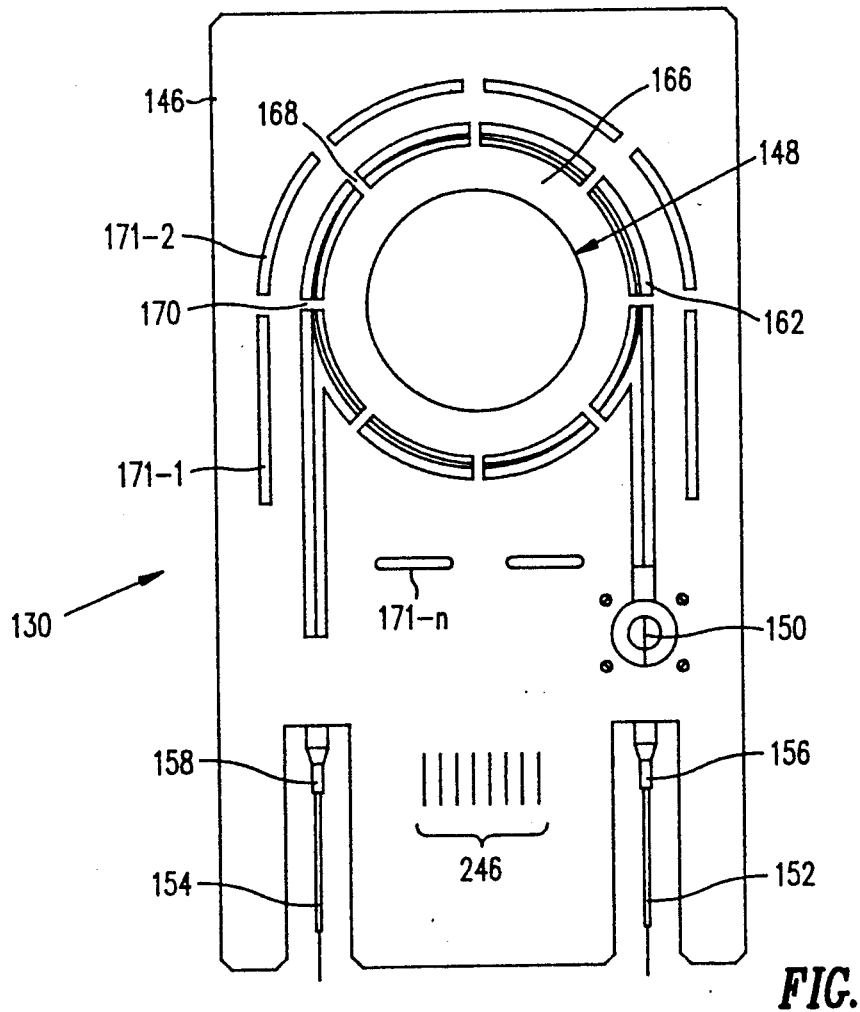
FIG. 4 shows an air cooled cartridge in accordance with the invention.

In accordance with the invention as shown in FIG. 4, air cooled cartridge 130 is marked with a bar code index 246 at a convenient location to identify the particular cassette. Also, additional information is included in bar code index 246. This information includes the length of capillary tube 162 in that particular air cooled cassette. The length of the tube is required as described above for determining electrical field strength, and electro-osmotic and electrophoretic mobilities and velocities. The length is also required to calculate the fluid-flow resistance in the capillary tube. The fluid-flow resistance is necessary for the system to determine automatically how long it takes for the capillary tube to be flushed with a given solution and what would be the approximate volume of sample loaded into the capillary tube for a given vacuum applied for a given period.

The system is automatically informed by reading bar code index 246 of the inside diameter of capillary tube 162. This is necessary for determining the fluid resistance of the capillary tube and the electrical resistance of the capillary tube for the above stated reasons.

The system is also informed automatically by bar code index 246 whether the tube is an open capillary tube, i.e. contains no gel, or is a closed tube, i.e. contains gel. This is important for hydrodynamic or vacuum type injections because the gel would be damaged or destroyed by application of a vacuum or hydrodynamic forces. Bar code index 246 also indicates whether the tube has its interior lined with a coating for purposes of knowing whether there is significant electro-osmotic flow in the capillary tube.

Also, as described above, each particular cartridge 130 is identified with its own particular number in bar code index 246 so that the system can automatically track the performance of each cartridge and/or capillary tube based on the separation efficiency for a given test.

Bar code index 246 on air cooled cartridge 130 is read in one embodiment of the invention by a conventional bar code reader (not shown) which is part of the electrophoresis instrument. Thus the bar code reader in the instrument reads bar code index 246 on a particular air cooled cartridge and provides the information in the index to the microprocessor and related computer software for the above described purposes.

Remote Optical Path

Figure 1:
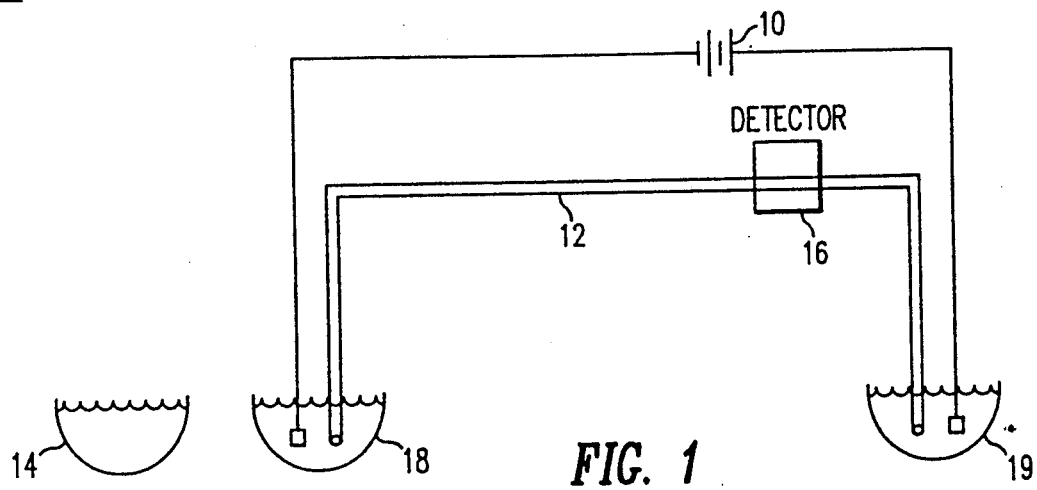
FIG. 1 shows a prior art electrophoresis apparatus.
Figure 2:
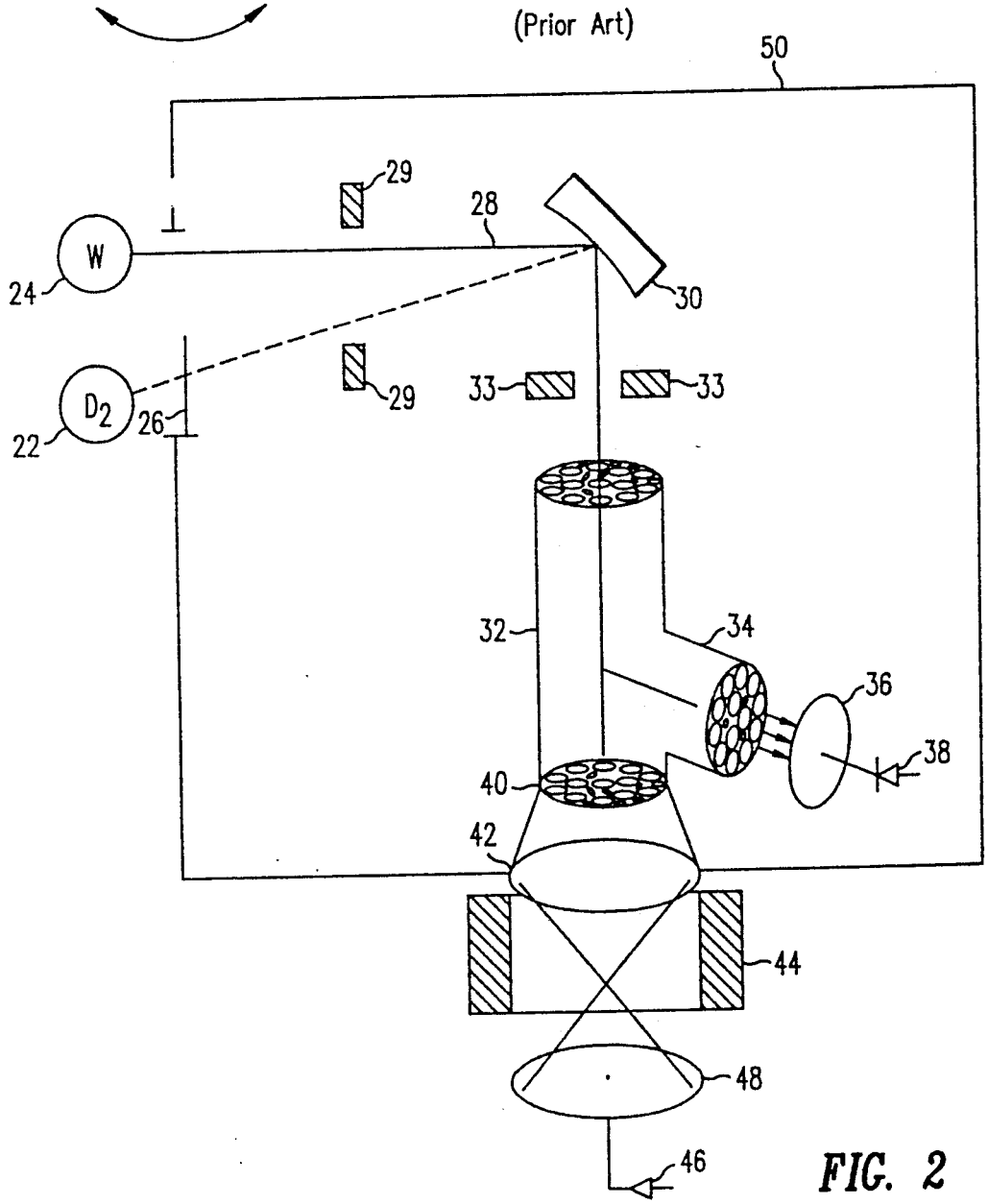
FIG. 2 shows a prior art optical path for the a UV-visible detector which may be used in the device of FIG. 1.
Figure 9A:
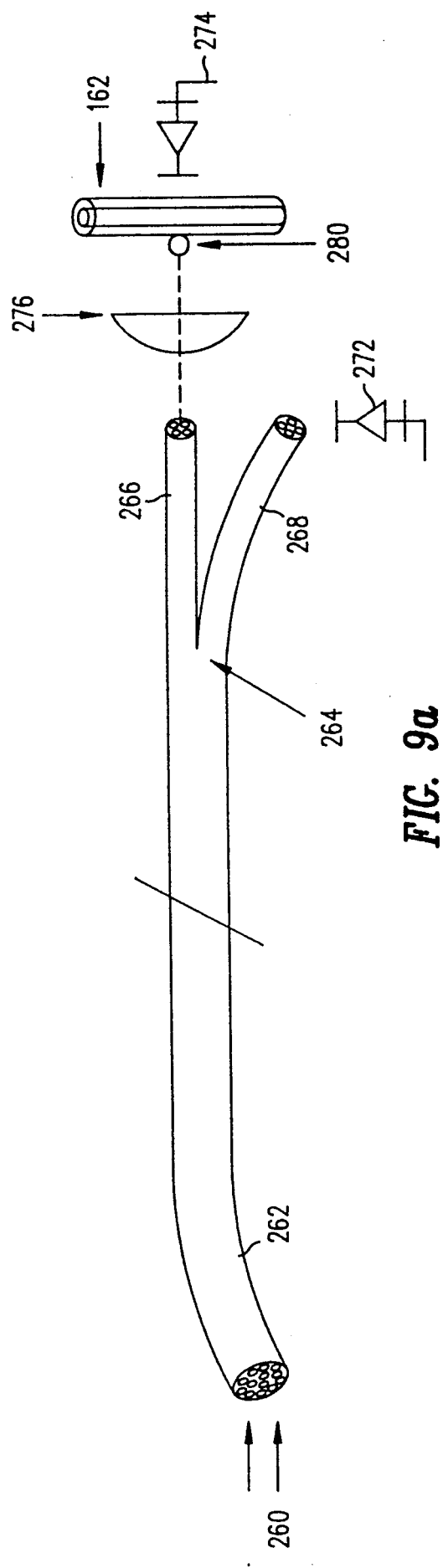
FIGS. 9(a) to 9(f) show a remote optical path in accordance with the invention.

The remote optical path as shown schematically in FIG. 9(a) includes a unique fiber optic beam splitter 120 (as in FIG. 3(c)) arrangement for detecting small sample volumes (down to about 100 picoliters) in a capillary. Light 260 is focused into a fiber optic bundle 262 from the exit slit of a conventional monochromator (including one or two light sources, a shutter, and a diffraction grating as in FIG. 1 and not shown here). The monochromator may be generating light of a given bandwidth for the purpose of UV-visible photometric absorbance detection, fluorescence detection, refractive index detection, as well as any other means of photometric detection. Light may also be focused into fiber optic bundle 262 from a coherent light source (laser) for the purpose of refractive index, fluorescence, thermal-optical-density detection, as well as other means of coherent light photometric detection. Fiber optic bundle 262 is remotely bifurcated at point 264 into a sample arm 266 and a reference arm 268. The light exiting from reference arm 268 impinges onto a reference photodetection device 272 located in the same environment as the sample photodetection device 274. Light emitting from sample arm 266 is focused using a plano-convex lens 276 into a second, spherical lens 280 in direct contact with the capillary 162.

The fibers of fiber optic sample arm 266 may be arranged in cross section in a circle, rectangle, square, trapezoid, or other parallelogram or triangular pattern in order to facilitate the focusing of the image into the center of the capillary. Sample photodetector 274 is placed directly behind capillary 162. The beam splitter housing self-aligns via locating hole 230 in the manifold 124 (see FIG. 8) and on the cartridge lens holder 150 (see FIG. 4). Spherical lens 280 is thus located in the cartridge lens holder 150, while the plano-convex lens 276, reference photodetector 272, and both ends of the fiber optic bundle 262 are housed in a retractable member (not shown) which slides into and out of the spherical lens holder 150 which is mounted on cartridge 130 (see FIG. 4).

This structure is advantageous in that remote transference of detection light in the common arm of a bifurcating fiber optic bundle greatly reduces the optical system's sensitivity to mechanical perturbations to the fiber optics. In this approach, light changes are simultaneously viewed by sample 274 and reference photodetectors 272 and are thus correctable.

Placement of both photodetectors 272, 274 in a similar environment reduces perturbations resulting from physico-mechanical variances in detection environments. The combination of lenses produces an image of appropriate size for small volume detection without any attendant loss of throughput. The mechanical layout of the system is such so that all optical elements are self-aligning.

Figure 9D:
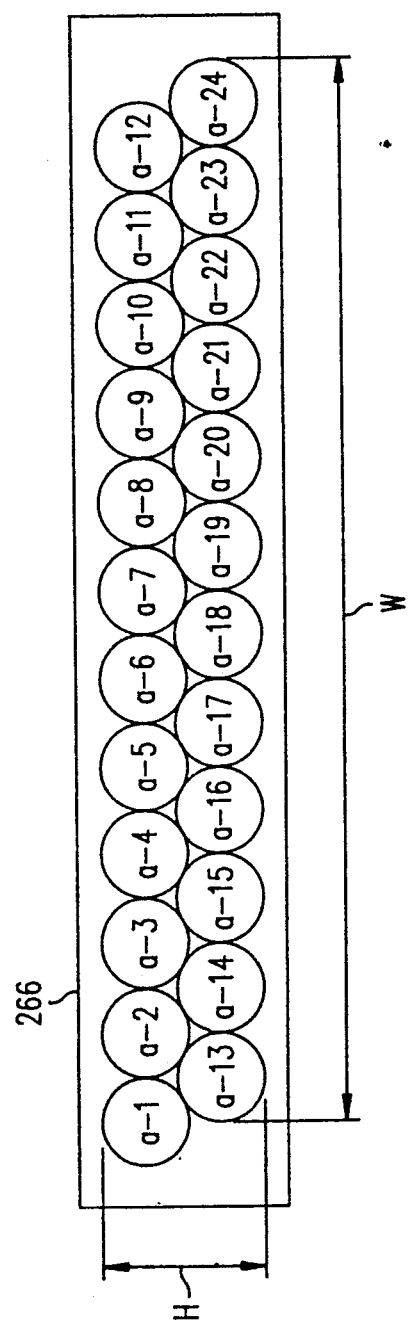
Figure 9B:
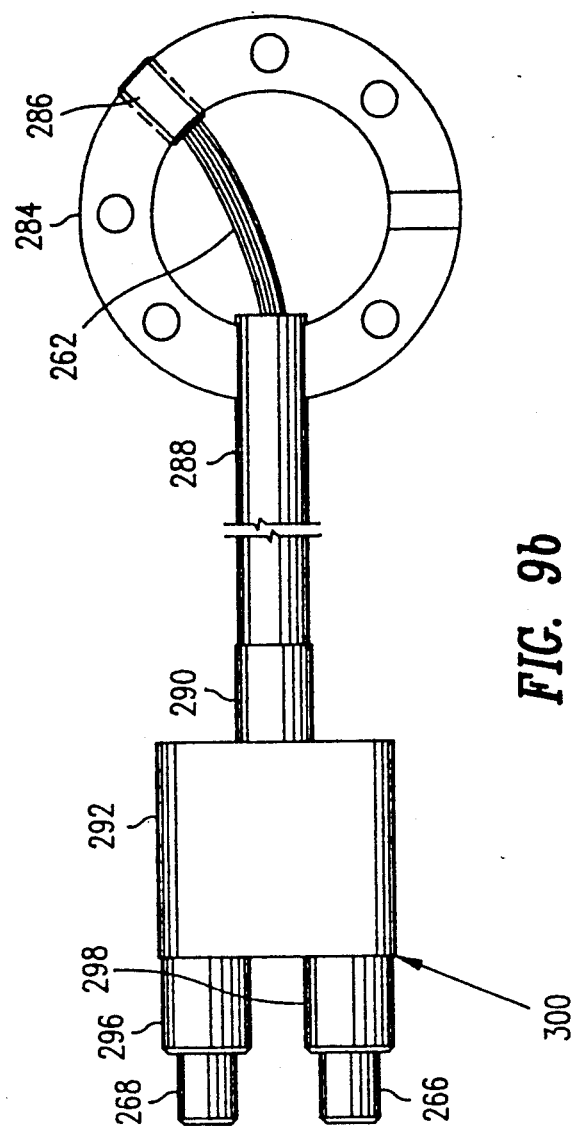
Figure 9C:
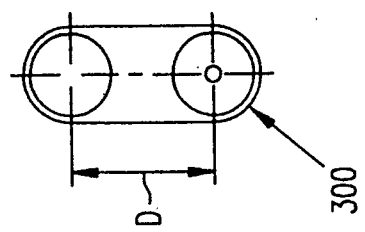

FIG. 9(b) shows detail of the optical path at its upper end down to the bifurcation point. Shown are beam splitter body 284, an insert 286 in body 284 to hold the optical fiber bundle 262, the optical fiber exterior PVC monocoil coating 288, PVC shrink tubing 290 over the optical fiber bundle, and a dual plug body 292. Optical fiber bundle 262 bifurcates into a reference arm connector 296 and sample arm connector 298, both connected mechanically by a connector 300. Connector 300 is shown in a side view in FIG. 9(c). A spacing "d" of about 1.094" (28 mm) is provided between the center of the reference arm 268 and sample arm 266. The short axis of the sample fiber bundle is parallel to the long axis of the capillary and perpendicular to a horizontal line defined between the center points of the sample and reference arms.

The above described structure is fastened together with 2039 type epoxy. A 360° twist is provided in the fibers in the common sector 288 to increase flexibility.

In accordance with the invention the cross-section shape of the sample fiber optic bundle 266 may be varied in accordance with the application. For instance, in the case where the light beam in the sample arm is to be transversely focused into a cylinder such as the capillary, it is most desirable to provide a rectangular cross-sectional shape light beam. Thereby the fiber optic bundle is provided in a rectangular or parallelogram shape. In another case when it is desirable to focus the sample light beam into a cylindrical flow cell as in a liquid chromatography detector, then it is desirable to have a circular shape of the cross-section of the light beam and thereby the fiber optics are bundled into a circle in cross-section.

FIG. 9(d) shows the optical fiber pattern in sample arm 266 in a rectangular cross sectional arrangement. The overall width w is about 3.05 mm; the height h is about 0.46 mm. Shown are optical fibers a-1, a-2, . . . , a-24.

Figure 9E:
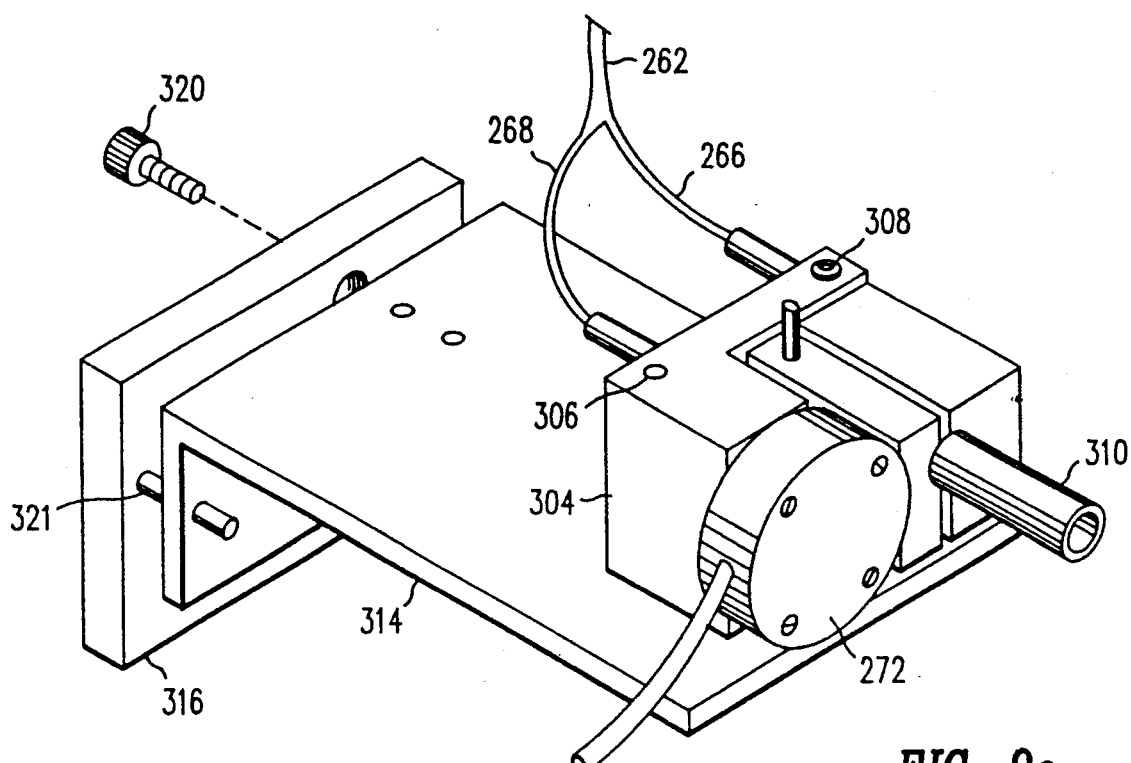

FIG. 9(e) shows the lower end of the remote optical path, with the beam splitter common trunk 262 bifurcating into the sample arm 266 and reference arm 268, both entering beam splitter block 304. Each arm 266, 268 is respectively attached to block 304 by a set screw 306, 308. The reference photodiode assembly 272 is shown, as is lens shroud 310 to carry the sample light beam to the sample cell (not shown). Beam splitter block 304 is fastened to platform 314, which is attached to support 316 by a set screw 320 and a set of dowels 321 (only one shown).

Figure 9F:
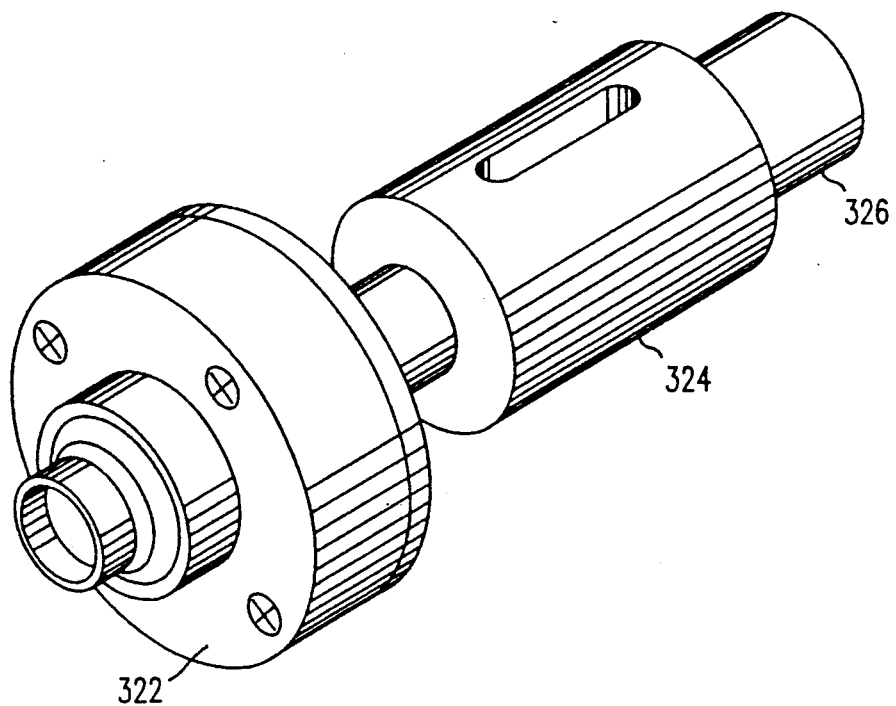

Detail of the sample photodiode assembly is shown in FIG. 9(f). Shown are the photodiode housing 322, spring assembly outer ring 324, and spring assembly inner ring 326.

Figure 10:
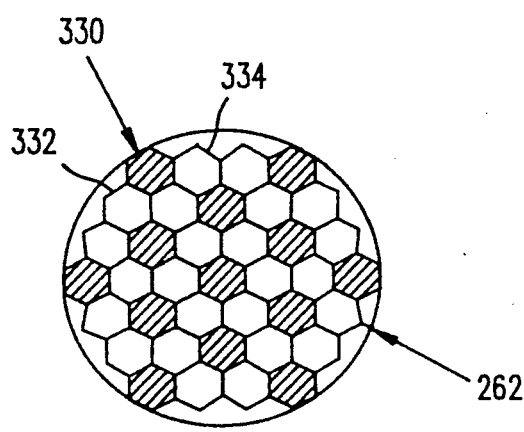
FIG. 10 shows detail of the fiber optic bundle used in the remote optical path.

FIG. 10 shows an end-on view of fiber optic bundle 262 showing that the fiber optic bundle 262 is composed of a number of triads of single optic fibers. Each triad consists of one reference type fiber 330 (shown by shading) and two sample type fibers 332, 334 (shown in white). The fibers themselves are identical between the sample and reference fibers. The designation of reference or sample merely indicates to which photodetector the optic fiber directs its light. The fiber triads are arranged in conjunction with each other so as when one moves from one reference plane at the entry portion of the beam splitter to another reference plane the triad is always conserved, so that at any angle the light is introduced to two sample and one reference optic fibers. Fiber optic bundle 262 in total includes in one embodiment 37 optic fibers. The diameter of common fiber optic bundle 262 is preferably about 0.067 inches (1.7 mm). This is a matter of design choice, and is not limiting in accordance with the invention. Twice as many sample fibers are provided as reference fibers, since the sample light beam must pass through the capillary tubing and other optics and thus there is more loss of throughput in the sample light beam.

In one embodiment of the invention, the fiber optic bundle is custom made. The optic fibers are ultraviolet transparent quartz approximately 200 microns in diameter, with a 20 micron thick cladding, and a 12.5 micron thick polyimid coating. The optical fibers are 200/220/245 superguide G type. The bundle is supported loosely by a 0.125 inch (3.1 mm) inside diameter teflon tube in a PVC monocoil outer jacket. The fiber optic bundle in one embodiment is provided by Highlight Fiber Optics in Caldwell, Id. The approximately overall length of the beam splitter is 28 inches (70 cm.). The point of bifurcation between the sample arm and the reference arm is at 26 inches (65 cm.) from the entry portion of the beam splitter.

Constant Capillary Electrical Resistance Temperature Control

Also in accordance with the invention, constant resistance cooling of the capillary is provided. As described above, the electrical resistance of the capillary provides a means of sensing the temperature of the capillary. Therefore, a method is provided for measuring and controlling the temperature of the capillary using the apparatus as shown in FIG. 6.

It is well known that the electrical resistance of the capillary is directly proportional to the capillary length and inversely proportional to the capillary radius squared. The solution electrical resistance is inversely proportional to the temperature of the solution and is inversely related to the specific conductivity of the solution in the capillary. This means that for a capillary of a given size and a given length containing a given solution, the electrical resistance is a direct function of the capillary temperature. In accordance with the invention, the high voltage power supply's current and voltage conventional sense lines are used to measure the electrical resistance of the capillary, and so in effect the capillary is used as a thermometer.

Figure 11:
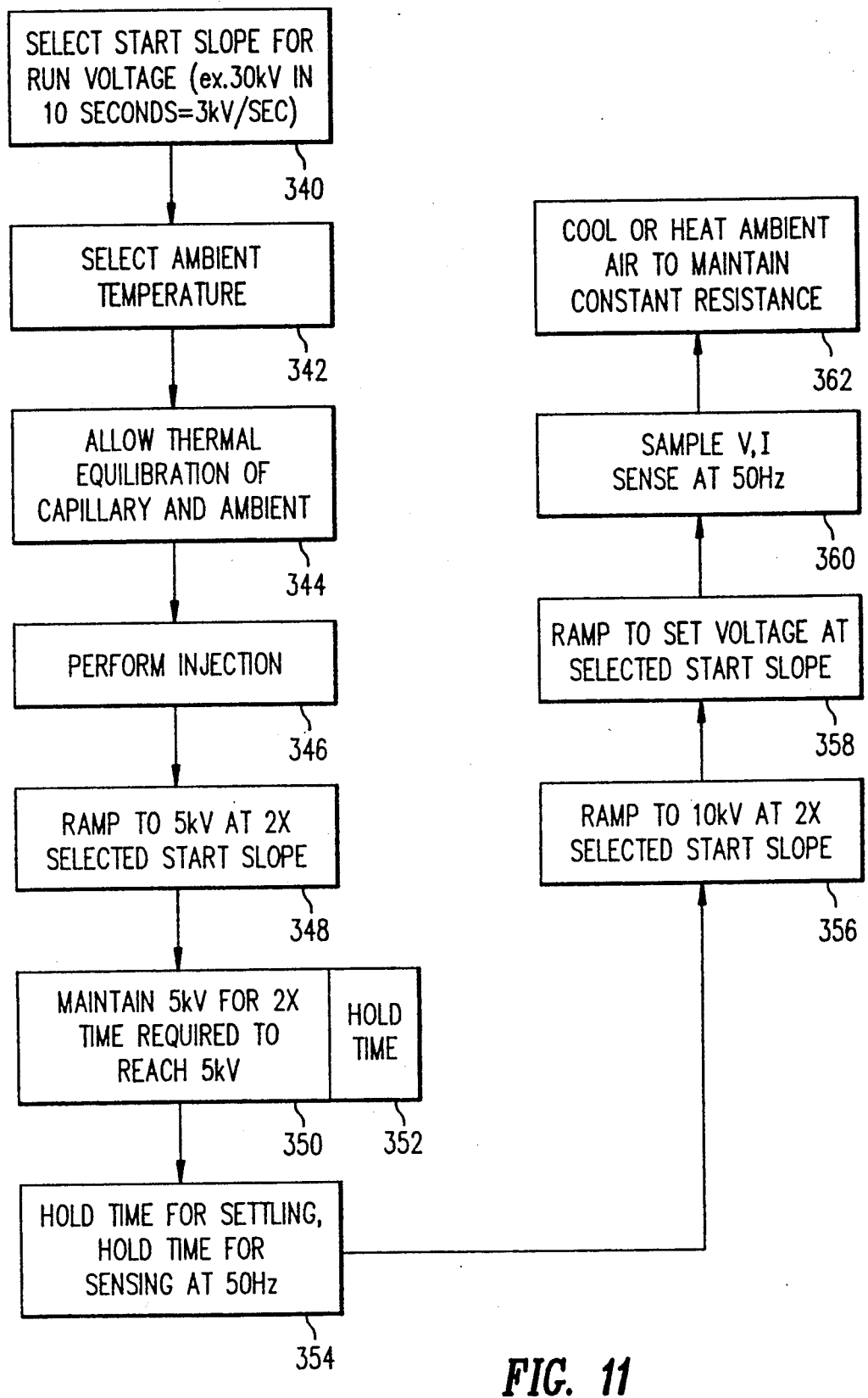
FIG. 11 is a flow chart showing a temperature control method in accordance with the invention.

A control procedure is provided to control the temperature of the capillary. This control procedure is a control program associated with the above-mentioned microprocessor 142 (see FIG. 7) resident in the electrophoresis instrument. The procedure for temperature control is shown in a flow chart in FIG. 11.

Figure 12:
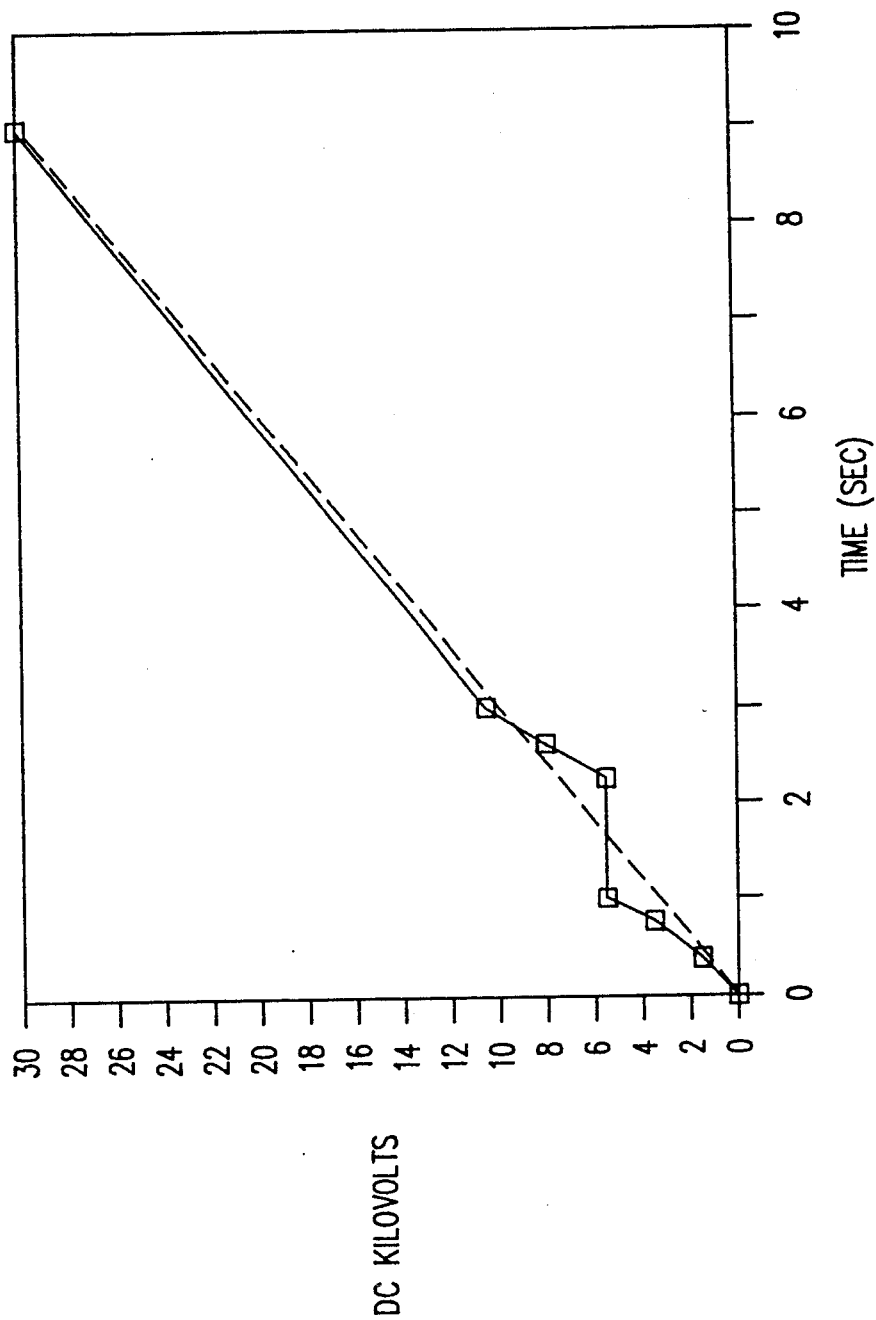
FIG. 12 shows a calibration plot for temperature control.

In accordance with the invention, the following steps are used in order to control temperature. First, a voltage start slope is selected at step 340. (See voltage vs. time plot, FIG. 12.) This is the rate (shown by the dotted line in FIG. 12) at which the ultimate separation voltage will be applied. For example, if the electrophoresis separation voltage of 30 KV is achieved in 10 seconds, then the start slope is 3 KV/second. Second, a set point ambient temperature is selected at step 342 for the capillary temperature as desired. This is done by the conventional method of monitoring the temperature of the air around the capillary tube and allowing sufficient time at step 344 for the heat transfer process to take place until the capillary tube approaches the target temperature and therefore the temperature in the capillary is very close to that of the surrounding air.

In the next step 346, the electrophoresis separation process in the capillary begins by performing a sample injection and beginning the run by increasing at step 348 both the current and the voltage of the electric power provided to the capillary. During the calibration phase the current and the voltage are increased at a particular steady rate, equivalent to two times the start slope at step 350. Capillary resistance is calculated during the hold time at step 352 (shown as about 0.8 to 2.4 seconds in FIG. 12) at 5 KV, at which level typically there is no significant joule heating. In the next step 354 the weighted average resistance or average resistance for the calibration period hold time is calculated. This calculated resistance is then attributed to the resistance of the system at the selected set point temperature. The voltage level is increased to 10 KV at twice the selected start slope in step 356. Then the voltage is further increased to the set voltage at the selected start slope in step 358.

The next phase in steps 360 to 362 is the temperature control phase. The resistance is monitored at step 360 at a particular duty cycle, i.e., for instance 50 times per second, by measuring the capillary current and voltage, and then in step 362 heat is either pumped into or out of the chamber in which the air cooled cartridge is housed by use of the previously described fan and Peltier device. Thus the electrical resistance of the capillary is maintained at a constant level, providing a constant temperature.

Buffer Gradient And Temperature Gradient Capillary Electrophoresis

Micellular electrophoretic chromatography is known in the art. (See Terabe, *J. of Microcolumn Techniques*, Vol 1, No. 3, 1989, p. 150.) This technique involves formation of a micell in the sample by providing a buffer solution containing amphophilic complexes which bind by non-polar or lipophillic attraction. They remain soluble in aqueous environments due to their polar moieties. For capillary, micellular electrokinetic chromatography, typically buffer solutions composed of acid or base salts (including but not limited to phosphate, tris, hepes, citrate, borate, amino acids, and other zwitter ionic buffers) in concentrations from 0.01 millimole to 500 millimole are used in conjunction with a detergent or other lipid-like moiety which forms micells. The micell producing agent (including but not limited to sodium dodecylsulfate, bile acids, etc.) is added until reaching minimal micell concentration for the given temperature.

In accordance with the invention, micellular, open tube separations take advantage of the differences in the partition coefficients of various solutes so that the higher the partition coefficient the longer the solutes stay in contact with the micell under the influence of the electric field in the electrophoresis instrument. Thus it is possible to separate neutral compounds on the basis of their partition coefficients. However, a problem arises in trying to separate solutes of similar partition coefficients or whose partition coefficients are so large that they co-migrate on the micells and are never separated. In buffer gradient electrophoresis, the buffer composition is changed over time and thus because the basic function of the partition coefficient is dependent on the two phases, polar and non-polar components (polar component being the buffer and the non-polar, the micell), the solubility of the solute in the buffer is changed. Thus as the lipophilicity of the buffer is increased, those compounds that have slightly lower partition coefficients will come off the micell. Thus the compounds are selectively removed from the micell as a function of time and thus contact the detector in the instrument and are observed.

Figure 13:
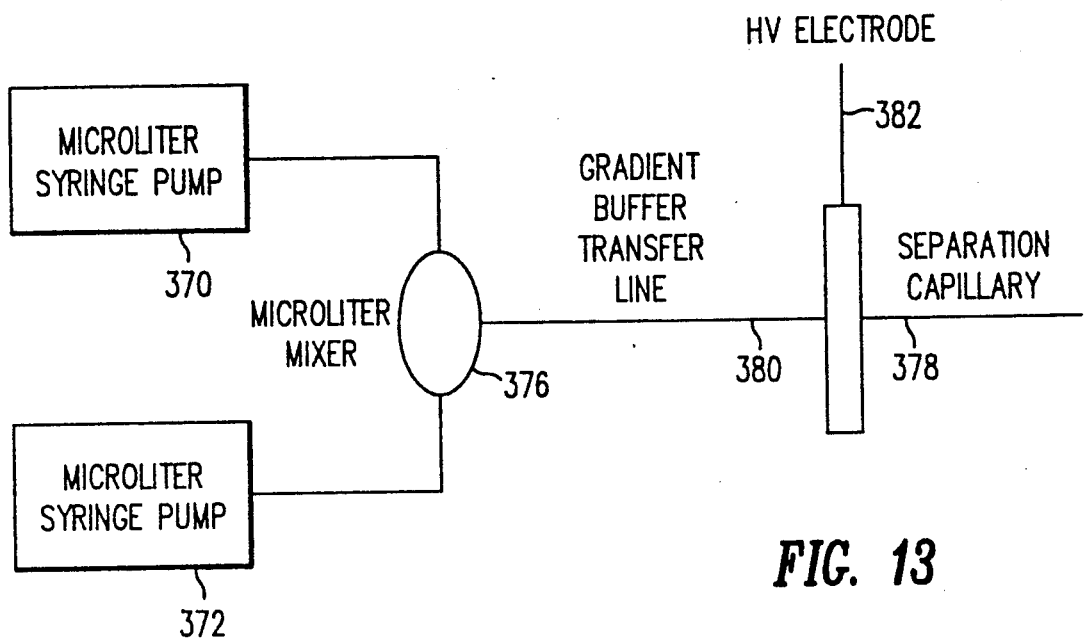
FIG. 13 shows a gradient micellular electrophoresis apparatus in accordance with the invention.

The gradient micellular chromatography apparatus is depicted in FIG. 13. A pair of conventional microliter syringe pumps 370, 372 are driven at different rates to displace different amounts of fluids which when mixed comprise the buffer. Mixing occurs in a conventional micromixer 376 and the resultant mixture is transported to separation capillary 378 via gradient buffer transfer line 380. High voltage electrode 382 creates an electric field in separation capillary 378.

Figure 14:
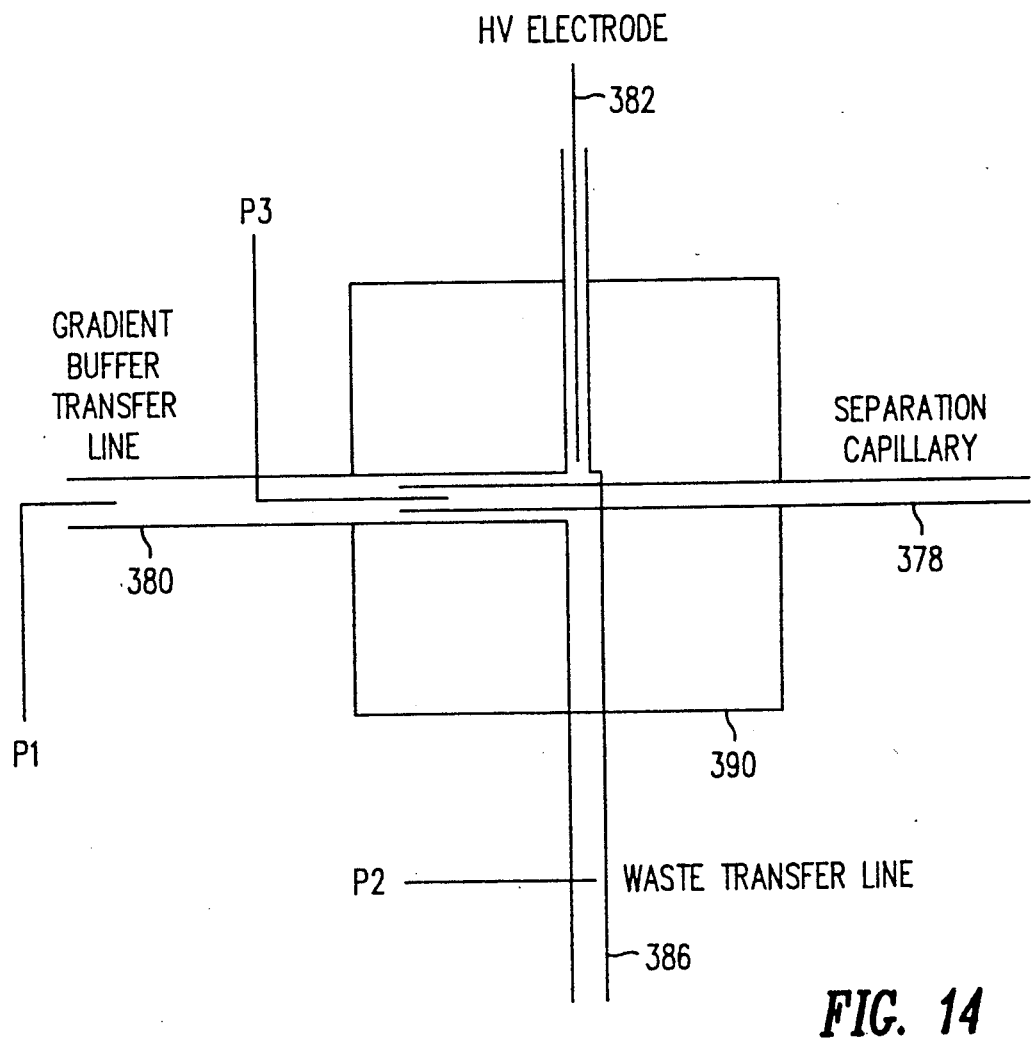
FIG. 14 shows detail of the gradient micellular electrophoresis apparatus.

Fluid from the gradient buffer transfer line 380 enters separation capillary 378 (see FIG. 14 showing detail of the device of FIG. 13) via electro-osmotic flow (and not parabolic pressure driven flow) as long as the pressure head at point P3 is much greater than that at point P2. The excess buffer exits via waste transfer line 386. Sufficient mixing response time is achieved using this split-flow approach.

The microliter pumps 370, 372, micromixer 376 and separation capillary 378 are either held at ground potential or enclosed in a Farraday cage 390 to protect against electrical shock.

In accordance with the invention, gradient micell electrophoresis may also be achieved by temperature programming. The Gibbs free energy of binding between the solute and micell is determined by the sum of the binding enthalpy and the temperature-entropy product ($\Delta G° = \Delta H° - T\Delta S°$). If $\Delta G°$ is negative, binding occurs. In thermal gradient micellular capillary electrophoresis, temperature is increased as a function of time. Consequently, the temperature-entropy product also increases. When the temperature-entropy product exceeds the enthalpy of solutemicell binding, the solute is released from the micell and thus migrates at a faster rate to the detector. In order for this process to be used in a reliable, reproducible manner, precise temperature control is required. Such control is possible using the previously described constant resistance cooling technique.

Electro-Osmotic Flow Using Automatic Neutral Marker

Figure 15:
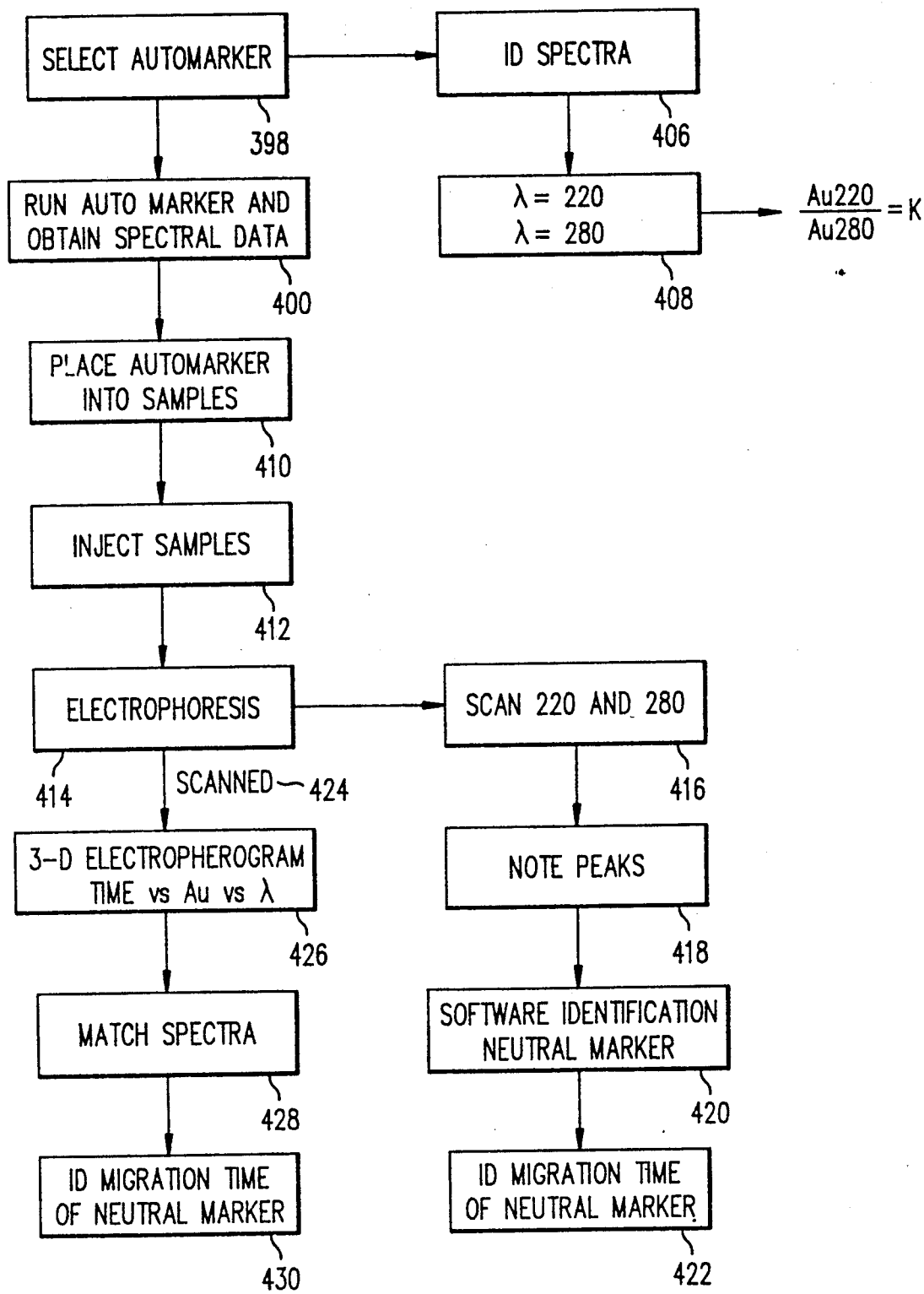
FIG. 15 is a flow chart showing use of a neutral marker in accordance with the invention.

In accordance with the invention, a method is implemented by use of the control program resident in the instrument's computer software for identification of neutral markers. This process is shown in flow chart form in FIG. 15.

In the first step 398, the user of the instrument selects a particular neutral marker substance. The neutral marker is selected as having a known spectrum and preferably having a spectrum greatly different from those of the solute molecules of interest. The selected neutral marker is then injected into the system in step 400 as a single component separation and its spectral characteristics measured. In the case of particular auto markers such as, for example, tryptophan at its pI (isoelectric pH), it is known that this auto marker will have an absorbance maximum at approximately 220 nanometers wavelength and a second absorbance maximum at approximately 280 nanometers wavelength as in step 406. Thus the system, based on data provided to it, will use the ratio of the absorbance at 220 nanometers to the absorbance at 280 nanometers to provide an identifying value at step 408 for this particular neutral marker. The selected neutral marker is then added in the appropriate concentration to the sample in step 410. A typical concentration is 0.1 milligram per milliliter. The samples containing the added-in neutral markers are then injected in step 412 into the capillary in the system.

In the next step 414, electrophoresis is conventionally performed. In accordance with one embodiment of the invention in steps 416 to 422, the spectrophotometric scanning is performed at step 416 at the two wavelengths of interest, 220 and 280 nanometers. In the next step 418 all peaks at these wavelengths are identified. Since other materials in the sample may also give peaks at 220 and 280 nanometers, the ratio of the absorbance at these two wavelengths is used to particularly identify at step 420 by a computer program the particular neutral marker tryptophan selected in the first step 422. Thus when this particular ratio is detected by the detector in the electrophoresis instrument, this identifies at step 422 the migration time of the neutral marker from the point of sample injection to the detector in the system.

In another embodiment of the invention in steps 424 to 430 the entire spectrum is scanned at a number of wavelengths at step 424. Then the system, by means of computer software, constructs at step 426 a three dimensional electropherogram of time versus absorbance versus wavelength. This electropherogram is then sliced perpendicular to the temporal, i.e. time axis, and then flipped around. This produces a spectrum of absorbance versus wavelength. This method allows identification of the spectrum associated with a particular neutral marker selected to provide a distinct spectrum. Thus when this particular spectrum is detected by the instrument in step 428, the time of detection determines the migration time of that particular neutral marker from the point of injection to the point of detection in the system in step 430. This method of scanning all wavelengths is more precise than the two wavelength method of steps 416 to 422 because it provides a better means of eliminating the problem of co-elution or comigration of solutes which are similar in their electrophoretic profiles to that of the neutral marker.

The velocity of electro-osmotic flow for both embodiments associated with the system is then determined by using the above-determined data from the neutral marker in steps 422 or 430. This determination is made in a post-run integration process (not shown). It is well known that electro-osmotic mobility is electro-osmotic velocity divided by electric field strength. Field strength is defined as voltage per column length. The velocity is the distance traveled from the beginning of the capillary at the point of injection to the point of detection of the neutral marker divided by the time required for this movement. Length L is the total length of the column from beginning to end and voltage is the applied voltage. Thus use of the neutral marker in detection hereof as described above allows calculation of the electro-osmotic velocity and of the electro-osmotic mobility.

The above description of the invention is illustrative and not limiting. Further modifications will be apparent to one of ordinary skill in the art in light of the disclosure and the appended claims.

We claim:

1. A cartridge for an electrophoresis instrument comprising:
   a housing;
   a bobbin supported in the housing;

a capillary tube wound around the bobbin;

a lens mounted on the housing adjacent to a portion of the capillary tube; and electrodes formed on the housing in electrical contact with two ends of the capillary tube;

wherein the housing defines a plurality of slots formed therethrough for cooling.

2. The device of claim 1, further comprising a bar code index formed on the housing for identifying the cartridge.

3. The device of claim 2, wherein the bar code index also includes at least one of: the length of the capillary tube, the inside diameter of the capillary tube, a configuration of the capillary tube, and an indication as to the nature of any coating on an inside portion of the capillary tube.

4. The device of claim 1, wherein the lens is a spherical lens.

* * * * *